(12) United States Patent
Yuk (10) Patent No.: US 8,923,957 B2
(45) Date of Patent: Dec. 30, 2014

(54) DATA CONVERSION IN ECG TECHNIQUES

(75) Inventor: Jongtae Yuk, Redmond, WA (US)

(73) Assignee: Verathon Inc., Bothell, WA (US)

( * ) Notice: Subject to any disclaimer, the term of this patent is extended or adjusted under 35 U.S.C. 154(b) by 21 days.

(21) Appl. No.: 13/184,213

(22) Filed: Jul. 15, 2011

(65) Prior Publication Data

US 2013/0018589 A1    Jan. 17, 2013

(51) Int. Cl.
*A61B 5/0402* (2006.01)
*A61B 5/0408* (2006.01)

(52) U.S. Cl.
CPC ....... *A61B 5/04028* (2013.01); *A61B 2562/046* (2013.01); *A61B 5/04082* (2013.01)
USPC ............................................. 600/509; 702/19

(58) Field of Classification Search
CPC .................. A61B 5/04021; A61B 5/04028
See application file for complete search history.

(56) References Cited

U.S. PATENT DOCUMENTS

| | | | | |
|---|---|---|---|---|
| 5,740,811 | A * | 4/1998 | Hedberg et al. | 600/510 |
| 6,119,035 | A * | 9/2000 | Wang | 600/509 |
| 2002/0035334 | A1* | 3/2002 | Meij et al. | 600/509 |
| 2002/0087088 | A1* | 7/2002 | Brodnick | 600/509 |
| 2006/0025695 | A1* | 2/2006 | Wei | 600/509 |

OTHER PUBLICATIONS

Dawson et al., Journal of Electrocardiology, vol. 42, pp. 622-630, 2009.*
Clifford et al., Computers in Cardiology, vol. 35, pp. 773-776, 2008.*
McClelland et al., American Journal of Cardiology, vol. 92, pp. 252-257, 2003.*
Paul Michalek, Thesis for School of Electrical Engineering and Computer Science, University of Central Florida, Abstract (p. ii), 2006.*
Fischer, G. Electrocardiogram (ECG) Mapping. Wiley Encyclopedia of Biomedical Engineering 1-15 (2006).*
Guillem, M. de la S. et al. Evaluation of lead selection methods for optimal reconstruction of body surface potentials. Journal of Electrocardiology 41, 26-34 (2008).*
Guillem, M. de la S. et al. How many leads are necessary for a reliable reconstruction of surface potentials during atrial fibrillation? IEEE Transactions on Information Technology in Biomedicine 13, 330-340 (2009).*
Wickens, T. D. The General Linear Model. 1-13 (2004).*
Finlay, D. D. et al. Synthesising the 12-lead electrocardiogram: Trends and challenges. Eur. J. Intern. Med. 18, 566-570 (2007).*

* cited by examiner

*Primary Examiner* — Soren Harward
(74) *Attorney, Agent, or Firm* — Foster Pepper PLLC; Richard A. Koske; P. G. Scott Born (57) ABSTRACT

A computer-implementable method includes generating a first set of input signals representing an X-lead ECG apparatus, generating a second set of input signals based on the first set and representing a Y-lead ECG apparatus, and generating to a display device a set of ECG traces and/or a diagnosis of acute myocardial infarction based on the second set. X and Y are integer values and Y is greater than X.

11 Claims, 7 Drawing Sheets

| 80-lead | 12-lead | 80-lead | 12-lead | 80-lead | 12-lead | 80-lead | 12-lead |
|---|---|---|---|---|---|---|---|
| 1 | RA | 21 | V2 | 41 | V3 | 61 | V5 |
| 2 | RA | 22 | V2 | 42 | V3 | 62 | V6 |
| 3 | V1 | 23 | V2 | 43 | V4 | 63 | V6 |
| 4 | V1 | 24 | V2 | 44 | V4 | 64 | RA |
| 5 | V1 | 25 | V3 | 45 | V4 | 65 | LA |
| 6 | V1 | 26 | V3 | 46 | LL | 66 | RA |
| 7 | V1 | 27 | V3 | 47 | LL | 67 | RA |
| 8 | RA | 28 | LA | 48 | V3 | 68 | RA |
| 9 | RA | 29 | V2 | 49 | V3 | 69 | RA |
| 10 | V1 | 30 | V2 | 50 | V4 | 70 | RA |
| 11 | V1 | 31 | V2 | 51 | V5 | 71 | RA |
| 12 | V1 | 32 | V2 | 52 | V5 | 72 | RA |
| 13 | V1 | 33 | V3 | 53 | V5 | 73 | RA |
| 14 | V1 | 34 | V3 | 54 | V5 | 74 | RA |
| 15 | V1 | 35 | V3 | 55 | LL | 75 | RA |
| 16 | V3 | 36 | V3 | 56 | V6 | 76 | RA |
| 17 | V3 | 37 | LL | 57 | V6 | 77 | RA |
| 18 | RA | 38 | V2 | 58 | V6 | RA | RA |
| 19 | LA | 39 | V2 | 59 | V6 | LA | LA |
| 20 | V2 | 40 | V3 | 60 | V5 | LL | LL |

| 80-lead | 12-lead | Ratio | 80-lead | 12-lead | Ratio | 80-lead | 12-lead | Ratio |
|---|---|---|---|---|---|---|---|---|
| 1 | VR | 2.2313 | 21 | V2 | 1.385 | 41 | V3 | 1.3997 | 61 | V5 | 2.0719 |
| 2 | VR | 4.4996 | 22 | V2 | 1 | 42 | V3 | 1.1814 | 62 | V6 | 2.2945 |
| 3 | V1 | 8.39 | 23 | V2 | 1.2228 | 43 | V4 | 0.8073 | 63 | V6 | 6.737 |
| 4 | V1 | 5.0402 | 24 | V2 | 1.7254 | 44 | V4 | 1 | 64 | VR | 2.3766 |
| 5 | V1 | 3.5675 | 25 | V3 | 2.28 | 45 | V4 | 1.3434 | 65 | VL | 1.6021 |
| 6 | V1 | 2.6013 | 26 | V3 | 3.0535 | 46 | I2 | 0.9754 | 66 | VR | 2.0341 |
| 7 | V1 | 1.1708 | 27 | I3 | 0.6995 | 47 | VF | 0.8639 | 67 | VR | 1.67 |
| 8 | VR | 1.8761 | 28 | VL | 1.3668 | 48 | V3 | 3.2847 | 68 | VR | 2.9918 |
| 9 | VR | 2.8743 | 29 | V2 | 4.838 | 49 | V3 | 2.2344 | 69 | VR | 1.8286 |
| 10 | V1 | 2.8147 | 30 | V2 | 2.13 | 50 | V4 | 1.3755 | 70 | VR | 1.5316 |
| 11 | V1 | 1.2562 | 31 | V2 | 1.3175 | 51 | V5 | 0.787 | 71 | VR | 1.4169 |
| 12 | V1 | 1 | 32 | V2 | 1.0437 | 52 | V5 | 0.9221 | 72 | VR | 3.1336 |
| 13 | V1 | 0.9383 | 33 | V3 | 1 | 53 | V5 | 1 | 73 | VR | 3.0844 |
| 14 | V1 | 1.0085 | 34 | V3 | 1.276 | 54 | V5 | 1.1807 | 74 | VR | 2.4983 |
| 15 | V1 | 1.1933 | 35 | V3 | 1.7019 | 55 | I2 | 1.2562 | 75 | VR | 2.3189 |
| 16 | V3 | 4.081 | 36 | V3 | 2.2691 | 56 | V6 | 1.395 | 76 | VR | 2.0222 |
| 17 | V3 | 3.4722 | 37 | VF | 0.851 | 57 | V6 | 1.1999 | 77 | VR | 1.7215 |
| 18 | VR | 2.712 | 38 | V2 | 8.4888 | 58 | V6 | 1.037 | RA | RA | 1 |
| 19 | VL | 0.8656 | 39 | V2 | 3.5428 | 59 | V6 | 1 | LA | LA | 1 |
| 20 | V2 | 2.7468 | 40 | V3 | 1.9474 | 60 | V5 | 1.9857 | LL | LL | 1 |

DATA CONVERSION IN ECG TECHNIQUES

BACKGROUND OF THE INVENTION

Sensor devices, such as electrocardiograph (ECG) devices, that can monitor bioelectric data from a body are known. An example of such a device is described in U.S. Pat. No. 6,055, 448. The apparatus described therein comprises an array of a plurality of N number of sensors in the form of electrode leads where N is an integer, each sensor of which is capable of detecting an electrical signal associated with components of a heartbeat. A known implementation of such an apparatus is an electrode vest employing 80 electrode leads.

A series of waveforms may be selected and generated to test and calibrate devices, such as ECG monitors, that respond to waveform signals. A conventional waveform-signal simulating device (i.e., ECG simulator) has one or more, typically digitized, waveforms in non-volatile memory, such as a read-only memory (ROM). The operator of the simulating device may request, via an operator interface, a digitized waveform that is then recalled from the memory and processed through a digital-to-analog converter (DAC). The converted signal, as an analog waveform signal, may then be transmitted to the device, such as an ECG monitor under test, that responds to the waveform for purposes of evaluation and calibration.

Unfortunately, an 80-lead ECG simulator is not available to simulate the above-referenced 80-lead vest; the typical implementation is a 12-lead ECG simulator.

SUMMARY OF THE INVENTION

In an embodiment, a computer-implementable method includes generating a first set of input signals representing an X-lead ECG apparatus, generating a second set of input signals based on the first set and representing a Y-lead ECG apparatus, and generating to a display device a set of ECG traces and/or a diagnosis of acute myocardial infarction based on the second set. X and Y are integer values and Y is greater than X.

BRIEF DESCRIPTION OF THE DRAWING

Preferred and alternative embodiments of the present invention are described in detail below with reference to the following figures.

DETAILED DESCRIPTION OF THE PREFERRED EMBODIMENT

Embodiments of the invention are operational with numerous general purpose or special purpose computing system environments or configurations. Examples of well known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

Embodiments of the invention may be described in the general context of computer-executable instructions, such as program modules, being executed by a computer and/or by computer-readable media on which such instructions or modules can be stored. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Embodiments of the invention may include or be implemented in a variety of computer readable media. Computer readable media can be any available media that can be accessed by a computer and includes both volatile and non-volatile media, removable and non-removable media. By way of example, and not limitation, computer readable media may comprise computer storage media and communication media. Computer storage media include volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

According to one or more embodiments, the combination of software or computer-executable instructions with a computer-readable medium results in the creation of a machine or apparatus. Similarly, the execution of software or computer-executable instructions by a processing device results in the creation of a machine or apparatus, which may be distinguishable from the processing device, itself, according to an embodiment.

Correspondingly, it is to be understood that a computer-readable medium is transformed by storing software or computer-executable instructions thereon. Likewise, a processing device is transformed in the course of executing software or computer-executable instructions. Additionally, it is to be understood that a first set of data input to a processing device during, or otherwise in association with, the execution of software or computer-executable instructions by the processing device is transformed into a second set of data as a consequence of such execution. This second data set may subsequently be stored, displayed, or otherwise communicated. Such transformation, alluded to in each of the above examples, may be a consequence of, or otherwise involve, the physical alteration of portions of a computer-readable medium. Such transformation, alluded to in each of the above examples, may also be a consequence of, or otherwise involve, the physical alteration of, for example, the states of registers and/or counters associated with a processing device during execution of software or computer-executable instructions by the processing device.

An embodiment of the invention is operable to convert a conventional 12-lead ECG simulator to an 80-lead ECG simulator. An embodiment of the invention enables conversion of 12-lead ECG signal data into 80-lead signal data. This, in turn, enables the execution of an 80-lead diagnostic algorithm for the detection of acute myocardial infarction (AMI). This algorithm assists in the interpretation of patient recordings.

Figure 1:
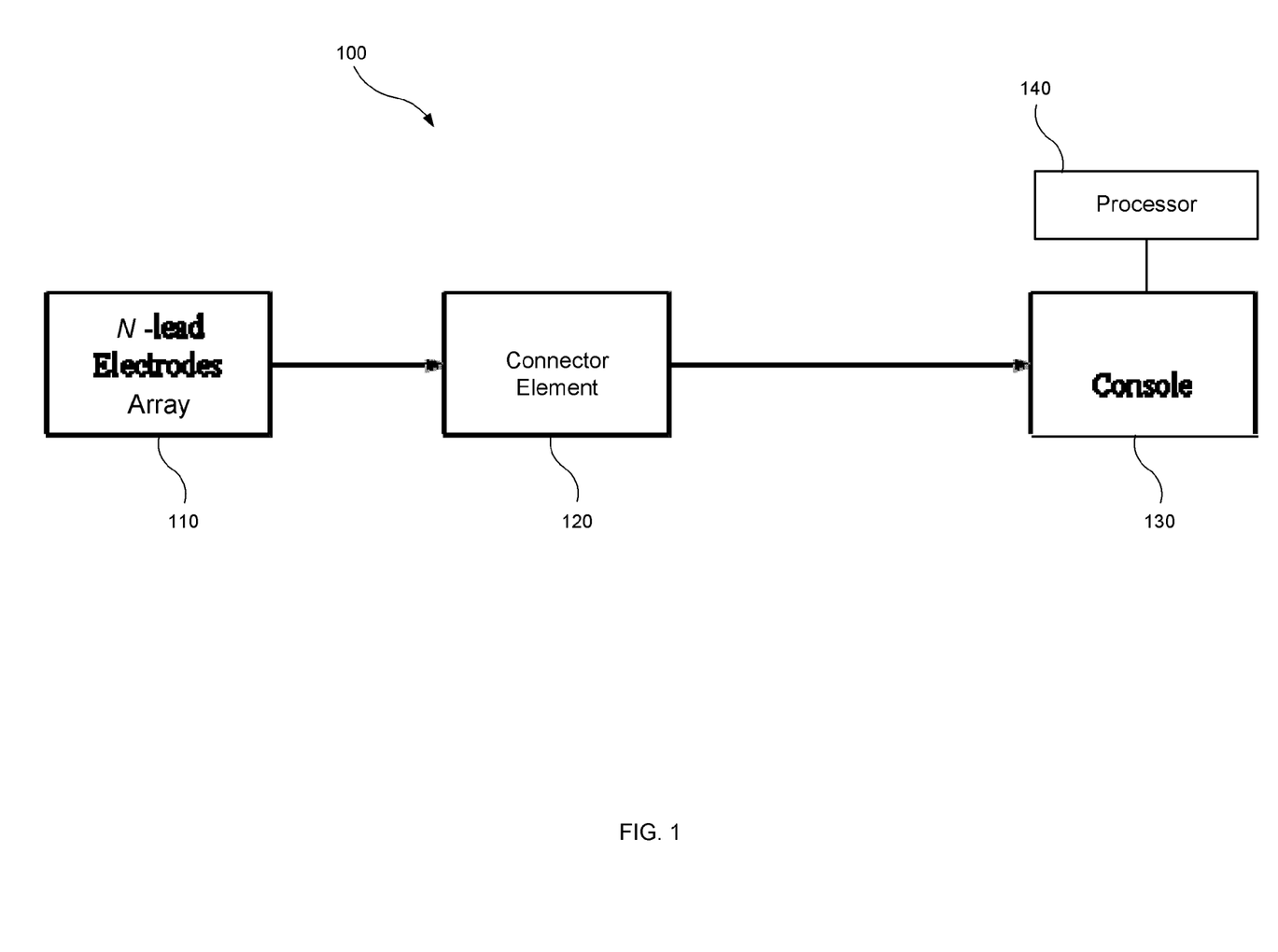
FIG. 1 is a high-level block diagram showing an ECG system 100 in accordance with an embodiment of the invention.

FIG. 1 is a high-level block diagram showing an ECG system 100 according to an embodiment or in which an embodiment may be implemented. System 100 includes an N-lead electrode array 110, a connector element 120, and a signal-monitoring console 130 including, or otherwise coupled to, a processing device (processor) 140.

ECG measuring systems generally apply 3 electrodes (to the chest or 10 electrodes (4 limbs and 6 specific points on the chest) to the skin, and, through a differential operational amplifier (OP-AMP), report signal differences between a selected pair of electric contacts or electrodes or between an electrode and a summed reference. The electrical activity thus monitored is generated by a sequence of ion movements in the heart that depolarize (release) and then repolarize (rebuild) an ionic charge distribution across cell membranes, which relates to actuation of contraction of the heart muscle.

By convention accepted in the art, a 12-lead ECG consists of lead pairings I, II, III, aVR, aVL, aVF, v1, v2, v3, v4, v5, and v6, where lead I reports the voltage difference between an electrode on the left arm (LA) and another on the right arm (RA); lead II left leg (LL) vs. right arm; lead III left arm vs. left leg; Lead aVR reports right arm vs. combined reference of left arm and left leg; aVL left arm vs. right arm and left leg; aVF left leg vs. left arm and right arm; and the v-leads (v1-v6, v for voltage) represent a series of prescribed positions across the front of the chest vs. the combined reference of left arm, right arm and feet. These relationships may be further illustrated by the following equations:

$$I = LA - RA \quad \text{(Eq. 1)}$$

$$II = LL - RA \quad \text{(Eq. 2)}$$

$$III = LL - LA \quad \text{(Eq. 3)}$$

$$aVR = RA - \tfrac{1}{2}(LA + LL) \quad \text{(Eq. 4)}$$

$$aVL = LA - \tfrac{1}{2}(RA + LL) \quad \text{(Eq. 5)}$$

$$aVF = LL - \tfrac{1}{2}(RA + LA) \quad \text{(Eq. 6)}$$

Figure 2:
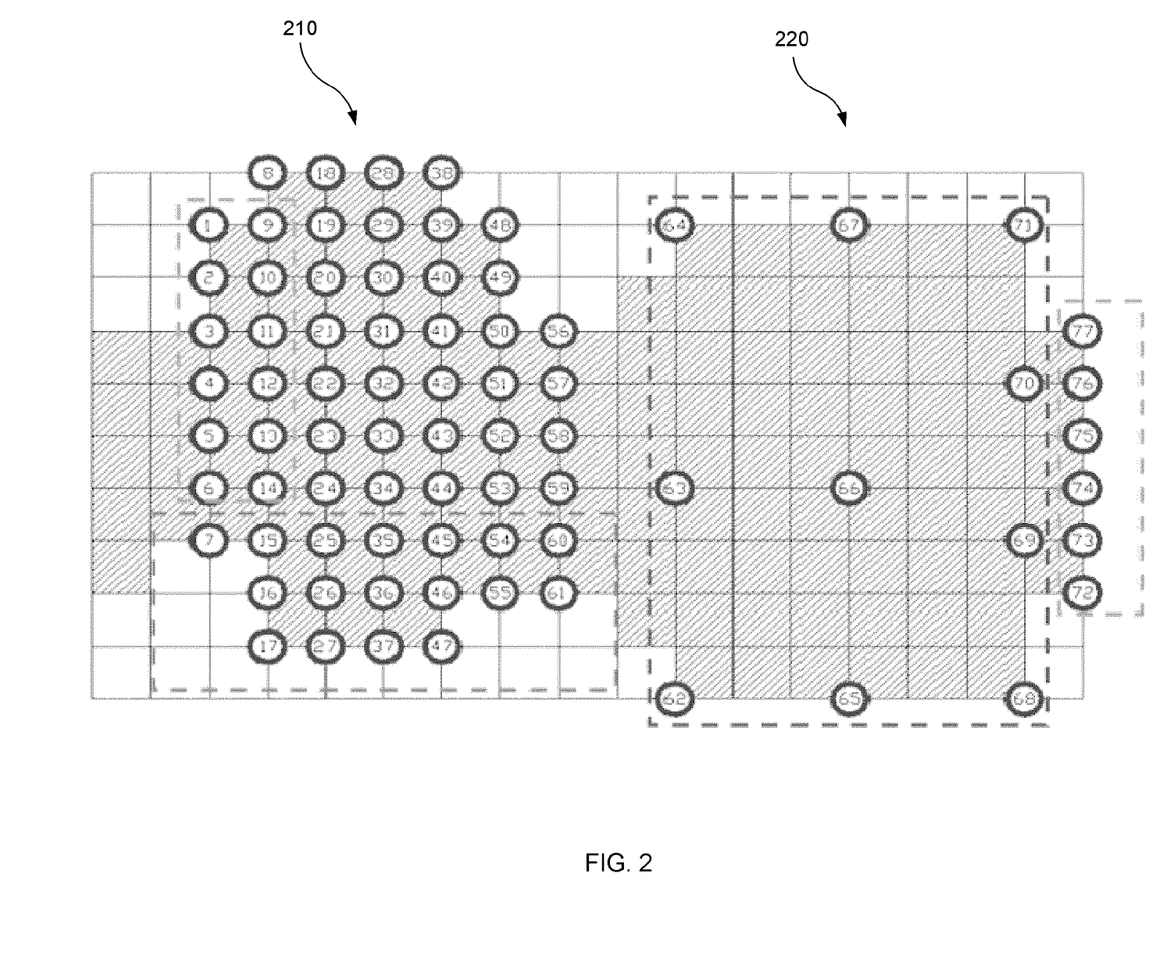
FIG. 2 is a schematic illustration of an arrangement of N electrodes in an array in accordance with an embodiment of the invention

FIG. 2 is a schematic illustration of the arrangement of an embodiment of the array 110 in the form of an 80-lead vest. In the illustrated embodiment, the array 110 includes an anterior sub-array 210 (i.e., leads 1-61) configured to be positioned on the front of a patient's torso and a posterior sub-array 220 (i.e., leads 62-77) configured to be positioned on the back of a patient's torso. The LA, RA and LL limb leads are not shown. The connector element 120 may be configured to provide a common electrical interface to the console 130 for both the anterior and posterior sub-arrays 210, 220.

In a first embodiment, the conversion inputs are six V-leads and three limb leads that can be obtained from the 12-lead ECG simulator (or, alternatively, from an actual 12-lead ECG sensor array). This first embodiment involves direct mapping from these 9 inputs to the 77 electrodes of the array 110.

Figure 3:
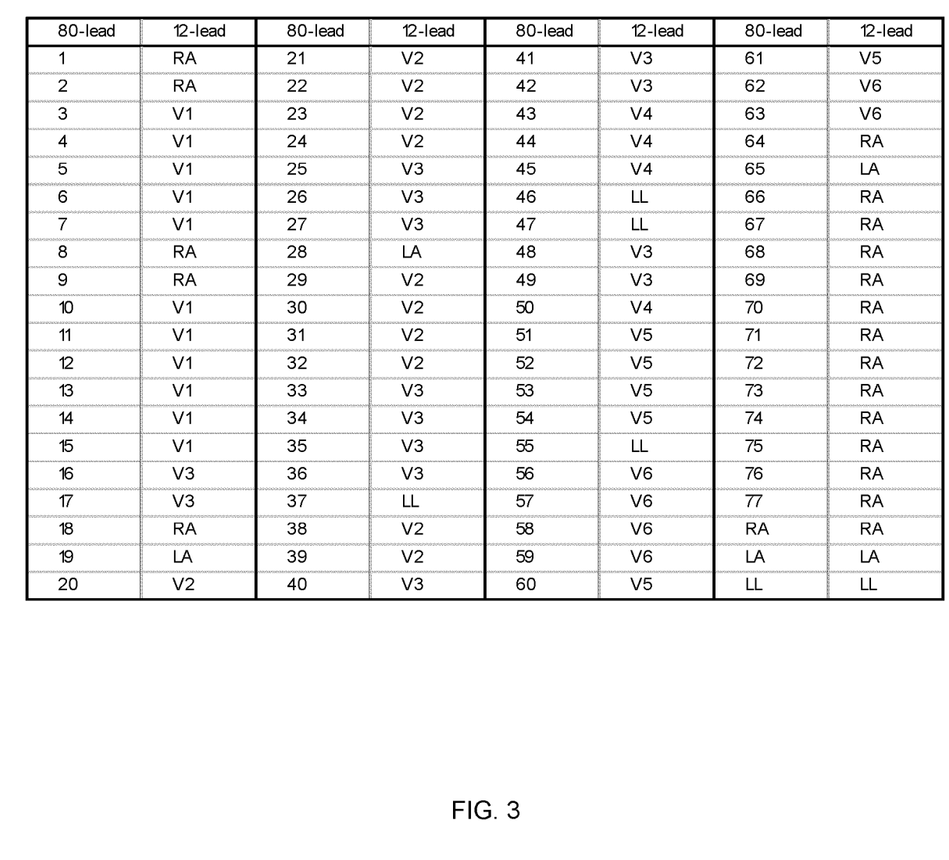
FIG. 3 illustrates a conversion table in accordance with an embodiment of the invention.
Figure 4:
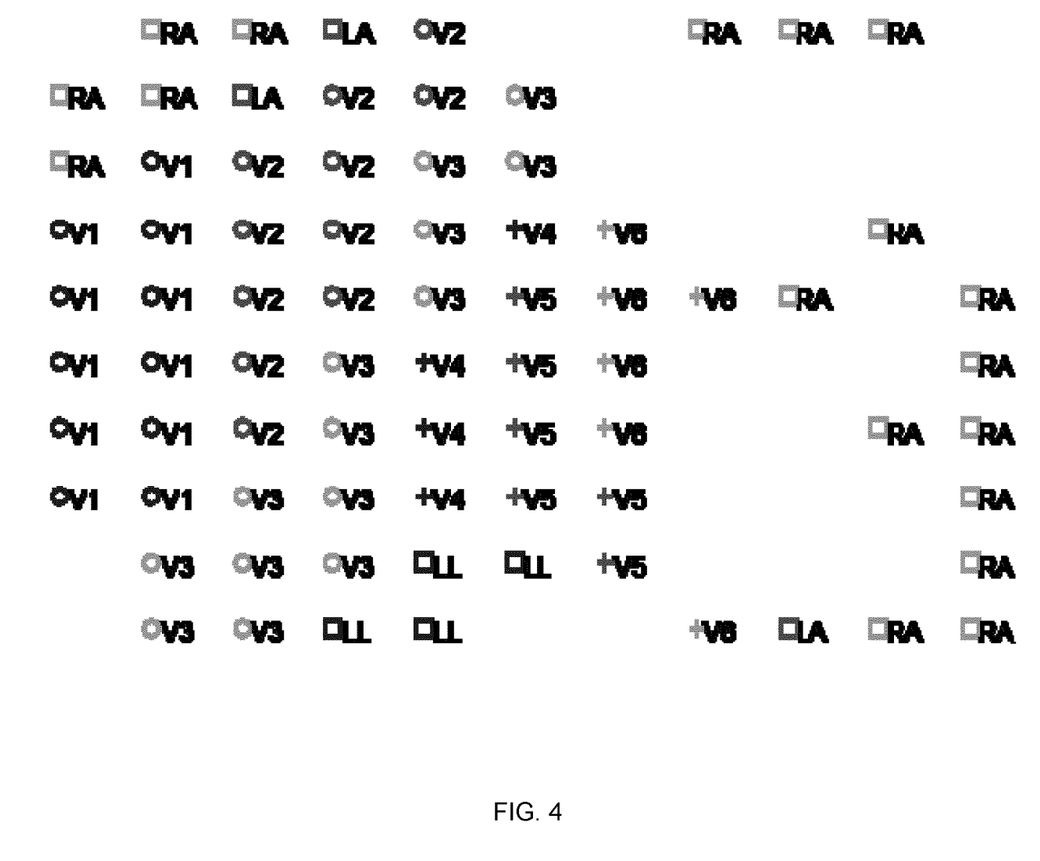
FIG. 4 illustrates a conversion table, as plotted with respect to the vest array 110 of FIG. 1, in accordance with an embodiment of the invention.

The conversion table from the 9 ECG waveforms generated by the 12-lead ECG simulator to a corresponding 80-lead input array, according to an embodiment, is illustrated in FIG. 3. This conversion table, as plotted with respect to the vest array 110, is illustrated in FIG. 4. The conversion table of FIG. 3 (and FIG. 5, discussed in further detail below) may be generated using a waveform correlation technique, an embodiment of which is illustrated in the flow chart of FIG. 7.

Figure 7:
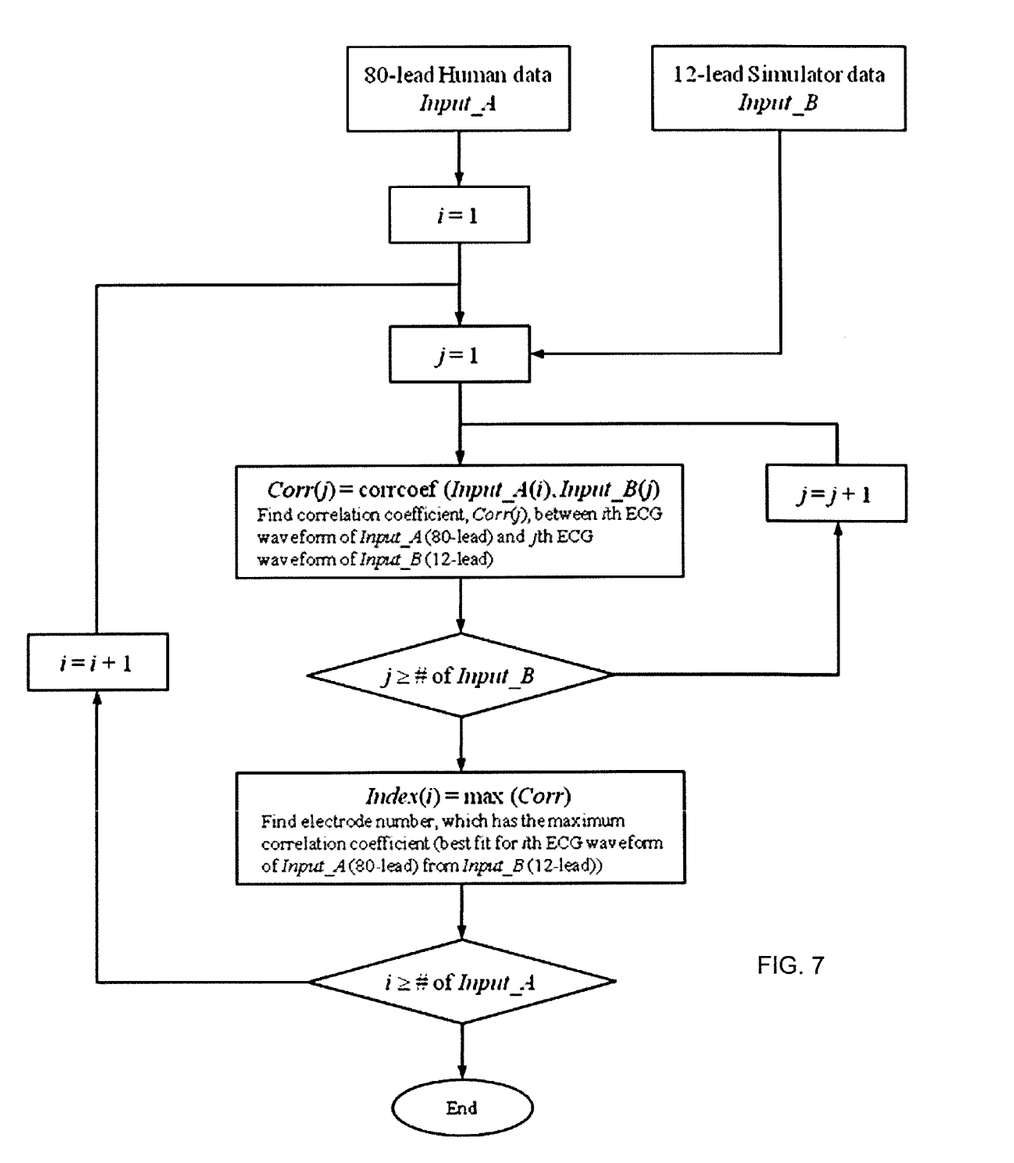
FIG. 7 illustrates a waveform-matching and correlation technique according to an embodiment.

To implement the technique illustrated in FIG. 7, according to an embodiment, data is collected by taking ECG readings from a 12-lead simulator or sensor array applied to a human subject. Such data collection produces a first set of waveforms, each waveform of the first set associated with a respective lead of the 12-lead simulator/array and having a distinctive set of characteristics (e.g., frequency, wavelength, etc.). Data is additionally collected by taking ECG readings from a human subject using an 80-lead array. This additional data collection produces a second set of waveforms, each waveform of the second set associated with a respective lead of the 80-lead array and having a distinctive set of characteristics. For each waveform generated by the 80-lead array, there is a corresponding one of the waveforms generated by the 12-lead simulator/array that is a "match" in terms of similarity of waveform characteristics. The technique illustrated in FIG. 7 provides a computational/automated approach to correlating the closest match between the respective waveforms of the first and second sets.

As a consequence of this conversion, an 80-lead ECG monitor may be tested and calibrated using a 12-lead ECG simulator. For example, the 80-lead monitor can display 80 ECG traces based solely on the 9 ECG waveforms generated by the 12-lead ECG simulator.

In an alternative embodiment, the conversion inputs are six V-leads (i.e., v1-v6, as discussed above herein) and six augmented leads (i.e., aVR, aVL, aVF, I, II, and III) that can be obtained from the 12-lead ECG sensor array (or, alternatively, from a 12-lead ECG simulator). The conversion in this alternative embodiment may be governed by the following equation:

$$Y = X/(\text{Ratio Value}) \quad \text{(Eq. 7)}$$

where, Y is the 80-lead signal amplitude and X is the amplitude of the corresponding 12-lead input.

Figure 5:
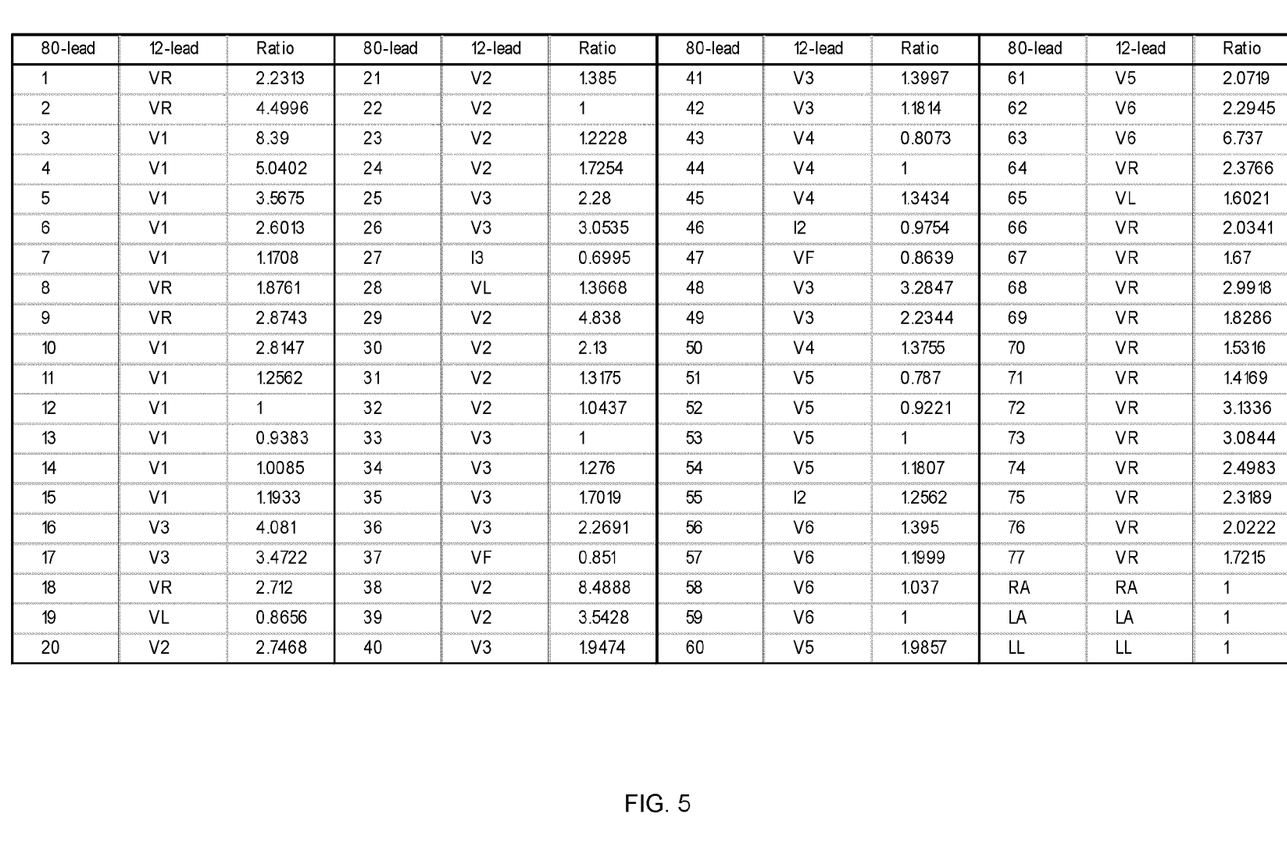
FIG. 5 illustrates a conversion table in accordance with an alternative embodiment of the invention.
Figure 6:
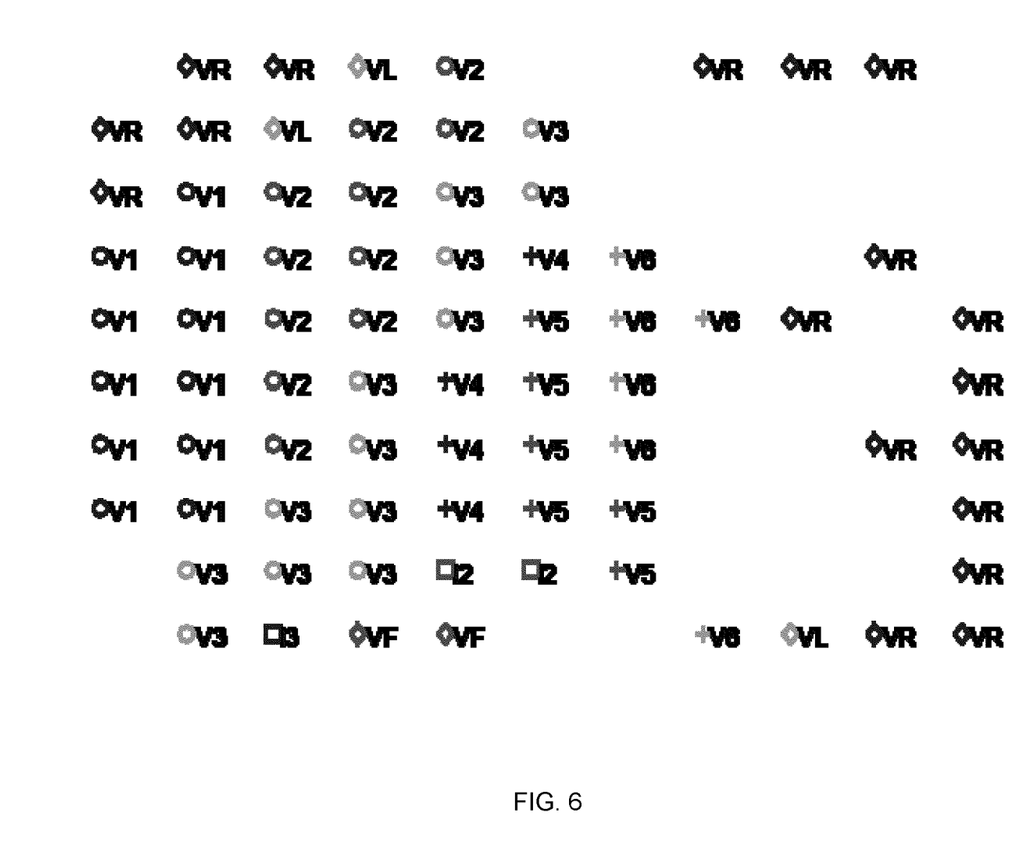
FIG. 6 illustrates a conversion table, as plotted with respect to the vest array 110 of FIG. 1, in accordance with the alternative embodiment of the invention.

The conversion table from the 12 lead inputs generated by the 12-lead ECG sensor array to a corresponding 80-lead input array, according to an embodiment, is illustrated in FIG. 5. This conversion table, as plotted with respect to the vest array 110, is illustrated in FIG. 6. As a consequence of this conversion, an 80-lead diagnostic algorithm for the detection of AMI may be generated using a 12-lead ECG sensor array. For example, the 80-lead monitor can generate a diagnosis of AMI based solely on the 12 lead inputs generated by the 12-lead ECG sensor array.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A non-transitory computer-readable medium including executable instructions that, when executed by a processing device, cause the processing device to perform a method comprising the steps of:

causing an X-lead electrocardiograph (ECG) apparatus to monitor electrical activity of a human subject, thereby generating a first set of input signals;

receiving the first set of input signals from the ECG apparatus;

accessing a set of conversion data comprising of a plurality of ratio values relating the signal amplitude of a single lead of the X-lead apparatus to the signal amplitude of a single lead of a Y-lead apparatus, wherein said ratio values are derived from ECG readings from at least one human subject;

generating a second set of input signals from the first set of input signals and the conversion data set, the second set representing a Y-lead ECG apparatus; and     generating to a display device a set of ECG traces based on the second set, wherein X and Y are integer values and Y is greater than X.

2. The medium of claim 1, wherein the value of X is 12.

3. The medium of claim 1, wherein the value of Y is 80.

4. The medium of claim 1, wherein the X-lead ECG apparatus comprises an ECG sensor array.

5. The medium of claim 1, wherein the set of ECG traces comprises Y ECG traces.

6. The medium of claim 1, wherein the conversion data is derived by correlating a first set of waveforms corresponding to ECG readings taken by an X-lead ECG apparatus with a second set of waveforms corresponding to ECG readings taken by a Y-lead ECG apparatus.

7. A non-transitory computer-readable medium including executable instructions that, when executed by a processing device, cause the processing device to perform a method comprising the steps of:

causing an X-lead electrocardiograph (ECG) apparatus to monitor electrical activity of a human subject, thereby generating a first set of input signals;

receiving the first set of input signals from the ECG apparatus;

accessing a set of conversion data comprising a plurality of ratio values derived from ECG readings of at least one human subject;

generating a second set of input signals representing a Y-lead ECG apparatus, wherein each value in the second set of input signals is generated by dividing the signal amplitude value of a single lead in the first set of input signals by a ratio value in the conversion data set; and     generating to a display device a diagnosis of acute myocardial infarction based on the second set, wherein X and Y are integer values and Y is greater than X.

8. The medium of claim 7, wherein the value of X is 12.

9. The medium of claim 7, wherein the value of Y is 80.

10. The medium of claim 7, wherein the X-lead ECG apparatus comprises an ECG sensor array.

11. The medium of claim 7, wherein the conversion data is derived by correlating a first set of waveforms corresponding to ECG readings taken by an X-lead ECG apparatus with a second set of waveforms corresponding to ECG readings taken by a Y-lead ECG apparatus.

* * * * *